United States Patent [19]

Hsu et al.

[11] Patent Number: 5,614,174

[45] Date of Patent: *Mar. 25, 1997

[54] STABILIZED DENTIFRICE COMPOSITIONS CONTAINING REACTIVE INGREDIENTS

[75] Inventors: Donald P. Hsu; David B. Viscio, both of Monmouth Junction, N.J.

[73] Assignee: Colgate Palmolive Company, New York, N.Y.

[*] Notice: The portion of the term of this patent subsequent to Nov. 14, 2014, has been disclaimed.

[21] Appl. No.: 339,371

[22] Filed: Nov. 14, 1994

[51] Int. Cl.$^6$ .................................. A61K 7/16; A61K 7/20

[52] U.S. Cl. .............................. 424/49; 424/53; 424/613

[58] Field of Search ........................................... 424/49–58

[56] References Cited

U.S. PATENT DOCUMENTS

| | | | |
|---|---|---|---|
| 2,501,145 | 3/1950 | Smith | 167/93 |
| 2,982,396 | 5/1961 | Shihadell | 206/47 |
| 3,250,680 | 5/1966 | Menkart et al. | 167/85 |
| 3,538,230 | 11/1970 | Pader et al. | 424/50 |
| 3,629,398 | 12/1971 | Schmitt | 424/43 |
| 3,689,637 | 9/1972 | Pader | 424/52 |
| 3,703,578 | 11/1972 | Cella et al. | 424/49 |
| 3,747,804 | 7/1973 | Raaf et al. | 222/1 |
| 3,885,028 | 5/1975 | Cella et al. | 424/52 |
| 3,980,767 | 9/1976 | Chown et al. | 424/52 |
| 4,098,435 | 7/1978 | Weyn | 222/94 |
| 4,132,771 | 1/1979 | Schreiber et al. | 424/52 |
| 4,358,437 | 11/1982 | Duke | 424/49 |
| 4,453,979 | 6/1984 | DeMasl et al. | 424/49 |
| 4,487,757 | 12/1984 | Kiozpeoplou | 424/49 |
| 4,565,691 | 1/1986 | Jackson | 424/52 |
| 4,568,534 | 2/1986 | Stier et al. | 424/49 |
| 4,582,701 | 4/1986 | Piechota | 424/52 |
| 4,814,160 | 3/1989 | Carter et al. | 424/49 |
| 4,828,824 | 5/1989 | Grollier | 424/52 |
| 4,857,303 | 8/1989 | Grollier | 424/52 |
| 5,071,638 | 12/1991 | Yoshie et al. | 424/49 |
| 5,256,402 | 10/1993 | Prencipe et al. | 424/53 |
| 5,264,205 | 11/1993 | Kelly et al. | 424/53 |
| 5,284,648 | 2/1994 | White et al. | 424/49 |
| 5,296,215 | 3/1994 | Burke et al. | 424/49 |
| 5,324,505 | 6/1994 | Kurnettka et al. | 424/49 |
| 5,372,803 | 12/1994 | Williams et al. | 424/53 |

*Primary Examiner*—Shep K. Rose
*Attorney, Agent, or Firm*—Paul Shapiro

[57] ABSTRACT

A dentifrice composition containing reactive ingredients such as peroxide and bicarbonate compounds which are stabilized to decomposition during storage by incorporating in the dentifrice composition about 1.0 to about 5.0% by weight of polyethylene glycol 2000.

15 Claims, No Drawings

STABILIZED DENTIFRICE COMPOSITIONS CONTAINING REACTIVE INGREDIENTS

Background of the Invention

1. Field of the Invention

The invention relates generally to a dentifrice composition containing reactive ingredients and more particularly to a dentifrice composition improved storage stability containing reactive peroxide and bicarbonate ingredients.

2. The Prior Art

It has been found to be very desirable to incorporate peroxide compounds in dentifrice compositions, the efficacy of peroxide compounds in oral hygiene having long been recognized. Such compounds have been proven effective in the treatment of gingivitis, periodontitis and in combating plaque. Additionally, peroxide compounds have been utilized for oral cosmetic purposes such as tooth whitening which results from bleaching and cleansing of tooth surfaces. A problem encountered with dentifrices formulated with peroxide compounds, is that the peroxide compounds tend to exhibit undesirable stability and decompose when subjected to a storage environment of abnormally high temperature e.g., temperatures in excess of 100° F.

This problem is exascerbated when peroxide compounds are utilized in combination with other ingredients of dentifrices which are reactive including alkaline abrasive agents such as sodium bicarbonate. The tendency of peroxide compounds to react with such other ingredients presents significant stability problems with respect to providing products which achieve adequate shelf life. Due to such instability the presence of the reactive ingredients causes gasing and bloating of the containers in which the dentifrice product is stored occur rendering the dentifrice product unacceptable for consumer use.

Examples of prior art attempts at providing stable peroxide containing dentifrices in which a second reactive ingredient is also included are found in the disclosures of U.S. Pat. No. 4,971,782, U.S. Pat. No. 4,897,258 and U.S. Pat. No. 4,837,008.

U.S. Pat. No. 4,837,008 discloses an aqueous dentifrice containing a peroxide and/or bicarbonate ingredient in which the ingredients are provided with a barrier coating to prevent reaction of the ingredients. A disadvantage to such dentifrice is that release of the ingredients for cleaning effect during use is diminished by the presence of the barrier coating.

U.S. Pat. No. 4,897,258 discloses an anhydrous dentifrice containing calcium peroxide and sodium bicarbonate wherein the anhydrous state of the dentifrice prevents reaction between the ingredients. A disadvantage to such dentifrice is that in spite of the anhydrous state of the dentifrice, limited storage stability is experienced.

U.S. Pat. No. 4,971,782 discloses an anhydrous dentifrice containing peroxide and bicarbonate ingredients in which one of the ingredients is coated with a water dissolvable coating and a peroxide stabilizer is included in the dentifrice to further enhance storage stability. In spite of the presence of the stabilizer, the dentifrice remains deficient in storage stability required for commercial use.

Because of the storage stability problems with dentifrices containing reactive ingredients such as peroxides and bicarbonate compounds, dentifrices containing either the peroxide or bicarbonate compound are separately maintained before use. For example, U.S. Pat. No. 4,687,663 discloses placing each of a peroxide gel and bicarbonate paste into separate compartments of a single two compartment container to avoid interaction between these ingredients before use. Such dual packaging devices are costly to manufacture and attempts at simultaneous even delivery of the two separate dentifrice components from the dual compartmented device is many times erratic.

There is therefore a need in the art for a dentifrice containing peroxide and other reactive ingredients such as bicarbonate salts which dentifrice remains stable during storage for extended periods of time and can be stored without provision for costly physical separation of components.

SUMMARY OF THE INVENTION

In accordance with the present invention, the stability of dentifrice compositions containing reactive ingredients such as peroxides and bicarbonate compounds which produce gaseous products in storage at elevated temperatures is substantially improved by incorporating in the dentifrice composition an effective stabilizing amount of polyethylene glycol 2000.

DESCRIPTION OF THE PREFERRED EMBODIMENTS

The vehicle used to prepare the stabilized dentifrice composition of the present invention is substantially anhydrous and includes a suitable humectant which is a substantially anhydrous viscous material, such as glycerin, sorbitol, polyethylene glycol, or any suitable mixture thereof. Limited amounts of water may be included in the vehicle of the dentifrice composition and preferably no more than about 9% by weight of the composition. When water is present in the dentifrice components in amounts in excess of about 9% by weight, the stability of the dentifrice composition is adversely affected.

As will be demonstrated hereinafter, the presence of relatively small amounts, e.g., about 1 to about 5% by weight of polyethylene glycol having a molecular weight of about 2000 as a humectant in a dentifrice composition containing reactive ingredients such as peroxide and bicarbonate compounds markedly improves the storage stability of the dentifrice. Such polyethylene glycol herein referred to as "polyethylene glycol 2000 or PEG 2000" is a nonionic polymer of ethylene oxide having an average molecular weight of 2000 and has the general formula

$$HOCH_2(CH_2OCH_2)_nCH_2OH$$

the number 2000 representing the average molecular weight and n representing the number of repeating -$CH_2OCH_2$- groups.

Other polyethylene glycols which can be used to advantage in the preparation of the dentifrice composition of the present invention include polyethylene glycol 400 and 600. It has been determined that the use of polyethylene glycol materials having molecular weights between 600 and 2000 in the preparation of the dentifrice composition of the present invention results in a dentifrice that is either too liquid, e.g. PEG 800, or too unstable, e.g. PEG 1350–1450, resulting in unacceptable gas generation. The use of polyethylene glycols having molecular weights greater than 2000, e.g., PEG 8000, results in a product that is, rheologically unacceptable, that is the dentifrice product is a non-extrudable "brick".

The proportion of vehicle used to prepare the dentifrice composition of the present invention is generally within the range of about 40 to about 70% by weight of of the paste or gel dentifrice component of this invention and preferably about 50 to about 65% by weight of the dentifrice component. Glycerin is present in the dentifrice vehicle of the present invention at a concentration of about 10 to about 60% by weight and preferably about 15 to about 40% by weight.

A surfactant is used in the preparation of dentifrice composition of the present invention to aid in prophylactic action and in the thorough dispersion of the dentifrice composition throughout the oral cavity when applied thereto as well as to improve the cosmetic acceptability and detersive and foaming properties of the dentifrice. Among the organic surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyi tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of clefin sulfonates, e.g. alkene sulfonates or hydroxalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium potassium or mono-, di or triethanol amine.

The surfactant is included in the dentifrice vehicle of the present invention at a concentration of about 0.5 to about 3.0% by weight and preferably about 1.0 to about 2.0% by weight.

Polishing agents are incorporated in dentifrice composition of the present invention and preferred polishing agents are siliceous materials, such as silica, and will normally have a mean particle size up to about 10 microns and a very high surface area, e.g. in the range of 150–750 square meters/gram. A preferred silica is a precipitated amorphous hydrated silica, such as Sorbosil AC-35 marketed by Crosfield Chemicals, or Zeodent 115 from J. M. Huber Company but other polishing agents may also be employed, including including peroxide reactive polishing agents such as sodium bicarbonate, calcium carbonate, as well as sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

Bicarbonate compounds, when included the dentifrice present invention, are included at a concentration of about 5 to about 20% by weight and preferably about 8 to about 15% by weight. The particle size of the bicarbonate compound can range from about 10 to about 300 microns although a particle size of 20–60 microns is preferred, the smaller particle size bicarbonate being more readily dispersed in the anhydrous vehicle.

The polishing agent is present in the dentifrice composition of the present invention at a concentration of about 10 to about 30% by weight and preferably about 5 to about 25% by weight.

Inorganic thickeners may be included in the dentifrices of the present invention and include fumed silicas such as Cab-o-sil available from Cabot Corporation, and thickening silicas including those available from W. R. Grace designated Sylox 15.

Organic thickeners such as natural and synthetic gums and colloids may also be incorporated in the dentifrice composition of the present invention. particularly when water in amounts up to about 9% by weight are present in the dentifrice component. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic or organic thickener may be incorporated in the compositions of the present invention at a concentration of about 0.05 to about 2% by weight and preferably about 0.1 to about 1.5% by weight.

The peroxide compound used as an ingredient in the dentifrice composition of the present invention is present in the dentifrice composition at a concentration of about 0.25 to about 5% by weight and preferably about 0.5 to about 2.0% by weight. Peroxide compounds suitable for use in the practice of the present invention include metal peroxides such as calcium peroxide, magnesium peroxide, barium, peroxide, and zinc peroxide.

Fluorine-providing salts having anti-caries efficacy may also be incorporated in the dentifrice of the present invention and are characterized by their ability to release fluoride ions in water. It is preferable to employ a water-soluble salt fluoride providing about 10–2,000 ppm of fluoride ion, and preferably about 1000–1500 ppm of fluoride ion. Among these materials are water-soluble inorganic metal salts, for example, sodium fluoride, potassium fluoride, sodium monofluorophosphate and sodium fluorosilicate. Sodium fluoride and sodium monofluorophosphate are preferred fluoride-providing salts.

Salts having anti-tartar efficacy including water soluble salts such as dialkali or tetra-alkali metal pyrophosphate salts such as $Na_4P_2O_7$, (TSPP) $K_4P_2O_7$, $Na_2K_2P_2O_7$, $Na_2H_2P_2O_7P_2O_7$ and $K_2H_2P_2O_7P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may be incorporated in the dentifrice products of the present invention preferably at a concentration of about 0.5 to about 8.0% by weight.

Colorants such as pigments and dyes may be used in the practice of the present invention. Pigments include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4- hydroxy-2-sulfoniumphenyl)-methylene}-[1-(N-ethyI-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the dentifrice composition in an amount from about 0.0005 percent to about 2 percent of the total weight of the dentifrice.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the dentifrice composition of this invention. Non-limiting examples thereof include preservatives, silicones and chlorophyll compounds, antibacterial agents such as chlorohexidene, halogenated diphenyl ethers such as Triclosan, desensitizing agents such as potassium nitrate and potassium citrate and mixtures thereof. These adjuvants are incorporated in the dentifrice components in amounts which do not substantially adversely affect the properties and characteristics desired, and are selected and used in proper amounts, depending upon the particular type of dentifrice component involved.

To prepare the dentifrice composition of the present invention, the humectants e.g. glycerin, polyethylene glycol 2000 and any other glycol ingredients and sweetner are dispersed in a conventional mixer until the mixture becomes a homogeneous gel phase. Into the gel phase are added a colorant and any tartar control agents such as TSPP or STPP or both and anti-caries agents such as sodium monofluorophosphate. These ingredients are mixed until a homogeneous phase is obtained. Thereafter the thickener, polishing agent, reactive ingredient such as peroxide, bicarbonate flavor and surfactant ingredients are added and the ingredients mixed at high speed under vacuum of about 20–100 mm Hg. The resultant product is a homogeneous, semi-solid, extrudable paste product.

The following examples illustrate this invention further. All proportions and amounts therein and elsewhere in this specification are by weight unless otherwise indicated.

EXAMPLE I

To demonstrate the stabilizing affect of PEG 2000 on the stability the compositions of the present invention during storage, dentifrice compositions of the present invention designated Composition A and B were prepared following the procedure previously described containing the ingredients listed in Table I below.

For purposes of contrast, the procedure of Example I was repeated to prepare a series of comparative compositions designated Compositions C–G in which PEG 2000 was not included as an ingredient. The ingredients of Compositions C–G are also listed in Table II below.

As a control, a Composition H which contained PEG 2000 but not $CaO_2$ or $NaHCO_3$ was also tested for gas stability. The ingredients of Composition H are also listed in Table I below.

TABLE I

| Dentifrice Ingredients | A | B | C | D | E | F | G | H |
|---|---|---|---|---|---|---|---|---|
| Glycerin | 20.25 | 20.25 | 20.25 | 19.50 | 20.25 | 18.50 | 18.50 | 20.25 |
| PEG 2000 | 3.50 | 3.50 | — | — | — | — | — | 3.50 |
| PEG 400 | 30.25 | 34.79 | 30.79 | 33.50 | 30.79 | 32.04 | — | 30.25 |
| PEG 1450 | — | — | 3.50 | — | — | — | — | — |
| PEG 3350 | — | — | — | — | 3.50 | — | — | — |
| PEG 600 | — | — | — | — | — | — | 32.04 | — |
| Na Saccharin | 0.50 | 0.50 | 0.50 | 0.50 | 0.50 | 0.50 | 0.50 | 0.50 |
| Xanthan | — | 1.00 | — | — | — | 1.0 | 1.0 | — |
| MFP | 0.80 | 0.76 | 0.76 | 0.80 | 0.76 | 0.76 | 0.76 | 0.80 |
| TSPP | 2.00 | 2.00 | 2.00 | 2.00 | 2.00 | 2.00 | 2.00 | 2.00 |
| NaTPP | 3.50 | 3.00 | 3.00 | 3.50 | 3.00 | 3.50 | 3.50 | 3.50 |
| $TiO_2$ | 3.00 | 3.00 | 3.00 | 3.00 | 3.00 | 3.0 | 3.00 | 3.00 |
| ZEO 115 | 18.50 | 18.50 | 18.50 | 15.50 | 18.50 | 20.00 | 20.00 | 18.50 |
| Sylo 15 | 3.00 | — | 3.00 | 7.00 | 3.00 | 4.00 | 4.00 | 3.00 |
| $NaHCO_3$ | 10.00 | 8.00 | 10.00 | 10.00 | 10.00 | 10.00 | 10.00 | — |
| $CaO_2$ | 2.00 | 2.0 | 2.00 | 2.00 | 2.00 | 2.0 | 2.00 | — |
| Flavor | 1.00 | 1.0 | 1.00 | 1.00 | 1.00 | 1.0 | 1.00 | 1.00 |
| SLS | 1.70 | 1.70 | 1.70 | 1.70 | 1.70 | 1.70 | 1.70 | 1.70 |

Dentifrices A-H listed in Table I were tested for stability to gas generation by adding 800 grams of each component to a sealed flask submerged in a water bath heated to 105° F. and connected to a manometer. The gas evolution detected by the manometer at 1 hour intervals was plotted on a graph in which the coordinates were gas evolution and time in hours. The slope of the best linear fit or regression of the data was then calculated and provided a Gas Generation Index. By this measurement, the higher the Gas Generation Index, the more unstable the product and the more prone it is to gas generation. The Gas Generation Index for Dentifrices A-H are listed in Table II below.

TABLE II

| Gas Generation Index of Dentifrice | | | | | | | |
|---|---|---|---|---|---|---|---|
| A | B | C | D | E | F | G | H |
| 0.18 | 0.23 | 0.46 | 4.18 | 1.63 | 2.67 | 4.40 | 0.06 |

The Gas Generation Index data recorded in Table II indicate that the peroxide/bicarbonate dentifrices containing 3.5% PEG 2000 (Dentifrices A-B) have substantially greater storage stability than dentifrice compositions in which PEG 2000 is not included in the dentifrice (Dentifrices C–G) and are substantially equal in stability to compositions which do not contain the gas generating compounds $NaHCO_3$ or $CaO_2$ (Dentifrice H).

EXAMPLE II

Dentifrices I and J having the composition listed in the Table III below were prepared following the procedure of Example I. The composition of Dentifrices I and J were substantially identical except that Dentifrice J was prepared without PEG 2000. Dentifrices I and J were then loaded into plastic laminate tubes, sealed and then aged at 105° F. and 120° F. for 1–4 days. The plastic laminate tubes and their contents were examined after the aging period. The aging results are summarized in Table IV below.

TABLE III

| Dentifrice | I Wt % | J Wt % |
| --- | --- | --- |
| Ingredient | | |
| Glycerin | 20.25 | 20.25 |
| PEG 2000 | 3.50 | — |
| PEG 400 | 34.29 | 32.79 |
| Na Saccharin | 0.50 | 0.50 |
| MFP | 0.76 | 0.76 |
| TSPP | 2.00 | 2.00 |
| NaTPP | 3.00 | 3.00 |
| TiO$_2$ | 2.00 | 2.00 |
| Zeodent 115 | 13.50 | 16.00 |
| Sylodent 15 | 3.50 | 3.00 |
| Na Bicarbonate | 12.00 | 15.00 |
| Ca Peroxide | 2.00 | 2.00 |
| Flavor | 1.00 | 1.00 |
| SLS | 1.70 | 1.70 |
| TOTAL | 100.00 | 100.00 |

TABLE IV

| | Aging at Elevated Temperatures | | | |
| --- | --- | --- | --- | --- |
| Dentifrice | 1 Day @ 105° F. | 4 Days @ 105° F. | 1 Day @ 120° F. | 4 Days @ 120° F. |
| I | No bubbles | No bubbles | Few bubbles | Few bubbles |
| J | Few bubbles | Lots of bubbles. Tube crimp split. | Lots of bubbles. Tube crimp split. | Lots of bubbles. Crimp split. Product oozing out. |

The results summarized in Table IV demonstrate that the presence of PEG in the dentifrice containing reactive peroxide and bicarbonate ingredients materially improves the aging stability of the dentifrice.

What is claimed is:

1. A dentifrice paste for cleaning teeth containing a reactive ingredient combination of calcium peroxide and sodium bicarbonate which is stabilized to interaction or decomposition during storage the paste being comprised of a substantially anhydrous vehicle which contains an effective stabilizing amount of at least about 1% by weight polyethylene glycol 2000, said vehicle containing as a humectant anhydrous glycerin, sorbitol, polyethylene glycol and mixtures thereof at a concentration of about 10 to about 60% by weight the composition containing limited amounts up to about 9% water, said sodium bicarbonate being included at a concentration of about 5 to about 20% by weight and said calcium peroxide being present at a concentration of about 0.25 to about 5% by weight.

2. The dentifrice composition of claim 1 wherein the reactive ingredient is a peroxide or bicarbonate compound.

3. The dentifrice composition of claim 2 wherein the bicarbonate compound is a sodium bicarbonate.

4. The dentifrice composition of claim 2 wherein the peroxide compound is calcium peroxide.

5. The composition of claim 1 wherein the reactive ingredient is a combination of a peroxide and bicarbonate compound.

6. The composition of claim 1 wherein the polyethylene glycol 2000 is present in the dentifrice composition at a concentration of about 1.0 to about 5.0% by weight.

7. A method for improving the storage stability of dentifrice paste compositions containing active ingredients which are a combination of calcium peroxide and sodium bicarbonate which method comprises preparing a substantially anhydrous vehicle in which the reactive ingredients are incorporated and then including in the substantially anhydrous vehicle an effective stabilizing amount of at least about 1% by weight polyethylene glycol 2000, said vehicle containing as a humectant anhydrous glycerin, sorbitol, polyethylene glycol and mixtures thereof at a concentration of about 10 to about 60% by weight the composition containing limited amounts up to about 9% by weight water, said sodium bicarbonate being present at a concentration of about 5 to about 20% by weight and said calcium peroxide being present at a concentration of about 0.25 to about 5% by weight.

8. The method of claim 7 wherein the reactive ingredient is a peroxide or bicarbonate compound.

9. The method of claim 8 wherein the peroxide compound is calcium peroxide.

10. The method of claim 8 wherein the bicarbonate compound is sodium bicarbonate.

11. The method of claim 7 wherein the reactive ingredient is a combination of a peroxide and bicarbonate compound.

12. The method of claim 7 wherein the reactive ingredient is a combination of calcium peroxide and sodium bicarbonate.

13. The method of claim 7 wherein the polyethylene glycol 2000 is present in the dentifrice composition at a concentration of about 1.0 to about 5.0% by weight.

14. The composition of claim 5 wherein the peroxide compound is calcium peroxide.

15. The composition of claim 5 wherein the bicarbonate compound is sodium bicarbonate.

* * * * *